United States Patent [19]

Wakamoto et al.

[11] Patent Number: 5,587,303
[45] Date of Patent: Dec. 24, 1996

[54] PRODUCTION PROCESS OF L-AMINO ACIDS WITH BACTERIA

[75] Inventors: Akiko Wakamoto; Osamu Takahashi; Keizo Furuhashi; Akira Miura, all of Toda, Japan

[73] Assignee: Nippon Mining Company, Ltd., Tokyo, Japan

[21] Appl. No.: 277,775

[22] Filed: Jul. 20, 1994

Related U.S. Application Data

[63] Continuation of Ser. No. 632,022, Dec. 21, 1990, abandoned, which is a continuation-in-part of Ser. No. 318,111, Mar. 2, 1989, abandoned.

[30] Foreign Application Priority Data

| Mar. 8, 1988 | [JP] | Japan | 63-052694 |
| Mar. 8, 1988 | [JP] | Japan | 63-052695 |
| Mar. 9, 1988 | [JP] | Japan | 63-055781 |
| Jun. 14, 1990 | [JP] | Japan | 2-155661 |
| Jul. 19, 1990 | [JP] | Japan | 2-191676 |
| Jul. 19, 1990 | [JP] | Japan | 2-191677 |

[51] Int. Cl.⁶ .......................... C12P 13/08; C12P 13/06
[52] U.S. Cl. .......................... 435/116; 435/115; 435/210; 435/106; 435/463; 435/412; 435/143
[58] Field of Search ............................... 435/106, 115, 435/116, 280, 863, 872, 843

[56] References Cited

U.S. PATENT DOCUMENTS

4,366,250  12/1982  Jallageas et al. ................. 435/280

FOREIGN PATENT DOCUMENTS

| 957965 | 11/1974 | Canada | 435/872 |
| 187680 | 7/1986 | European Pat. Off. | |
| 2245585 | 9/1973 | France | C07B 29/02 |
| 8607386 | 12/1986 | WIPO | C12P 41/00 |

OTHER PUBLICATIONS

Rogosa et al, "Actinomycete and Related Organisms", *Bergey's Manual of Determinative Bacteriology*, Buchanan et al ed., pp. 599–602, 658–659, 1974.

Good fellow et al, "The Biology of the Actinomycetes", 1984 pp. 14–17 and 80–81.

Chemical Abstracts, vol. 105, No. 7; Aug. '86 p. 513; Abst. No. 59419h.

*Primary Examiner*—Irene Marx
*Attorney, Agent, or Firm*—Schmeiser, Olsen & Watts

[57] ABSTRACT

A production process of optically active amino acids comprising causing a microorganism belonging to Rhodococcus, Mycobacterium, Arthrobacter, Nocardiopsis or Bacillus sp. and having nitrile-hydrolyzing activity to act on a nitrile or derivative thereof.

14 Claims, No Drawings

PRODUCTION PROCESS OF L-AMINO ACIDS WITH BACTERIA

This application is a continuation of application Ser. No. 07/632,022, Dec. 21, 1990 now abandoned, which is a continuation-in-part of applicants' earlier application Ser. No. 07/318,111 filed on Mar. 2, 1989 directed to a Production Process of L-α Amino Acids, now abandoned.

BACKGROUND OF THE INVENTION

This invention relates to a process for the production of optically active amino acids from nitrile compounds, particularly from racemic α-aminonitrile compounds or derivatives thereof by making use of microorganisms.

Optically active amino acids such as L-α-amino acids and D-α-amino acids are important chemical substances useful in a variety of fields such as foods, feeds, pharmaceuticals and cosmetics.

Conventionally, the fermentation, synthetic, enzymatic and extraction processes have been known to produce these optically active amino acids. Among these processes, the synthetic process comprises synthesizing first DL-α-amino acids in accordance with the Strecker process or a modification process thereof and then subjecting the amino acids to optical resolution to produce L-α-amino acids. In the optical resolution, the enzymatic process using aminoacylase or similar processes have been employed (Kagaku Zokan 97, Progress of Asymmetric Synthesis and Optical Resolution, Kagakudojin, 1982, p. 175).

However, the production of L-α-amino acids according to the above-described synthetic process requires increased costs in the stage of optical resolution. For such economical reasons, the process has recently suffered gradual share reduction in the production of amino acids.

An attempt has also been made reportedly to produce α-amino acids from DL-α-aminonitriles, which are intermediates in the synthesis of α-amino acids according to the aforementioned Strecker process and represented by the following general formula:

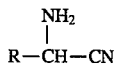

wherein R is an alkyl group, phenyl group or the like, by making use of microorganisms [Y. Fukuda et al., J. Ferment. Technol. 49, 1101 (1971)].

According to this report, however, DL-α-aminopropionitrile and DL-α-aminoisovaleronitrile are hydrolyzed in the presence of microorganisms belonging to Corynebacterium sp. to produce respectively DL-alanine and DL-valine, and therefore L-α-amino acids can not be obtained directly. It has also been reported that amino acids are produced by the hydrolysis of DL-α-aminonitriles in the presence of Brevibacterium sp. R312 [J. C. Jallageas et al., Adv. Biochem. Engineer. 14, 1 (1980)]. According to the report, only DL-α-amino acids are obtainable from DL-α-aminonitriles. In this connection, although the above report discloses a simultaneous production of L-α-amino acids and D-α-amino acid amides from DL-α-aminonitriles by the use of Brevibacterium sp. A4, a mutant obtained from Brevibacterium sp. R312, no description has been found with regard to the direct and exclusive production of L-α-amino acids from DL-α-aminonitriles. Further, this process necessarily involves such complex operation of separating an L-α-amino acid from a D-α-amino acid amide and hence is unfavored.

It has also been disclosed to produce amino acids by irradiating light to the reaction system before completion of the microbiological hydration of DL-α-aminonitrile compounds (Japanese Patent Laid-Open No. 162191/1986). However, only DL-α-amino acids are obtainable by this process. Thus, no report has so far been made to produce L-α-amino acids directly from racemic α-aminonitrile compounds.

As processes for producing D-α-amino acids, it has been known to produce, for example, D-alanine by reacting 5-substituted hydantoin with D-hydantoinase (Japanese Patent Publication No. 1909/1981), by reacting N-acetyl-D-alanine with D-aminoacylase (Japanese Patent Publication No. 36035/1978), or by reacting an amino acid amide with a microorganism having the activity of D-amino acid amide hydrolysis (Japanese Patent Laid-Open No. 274690/1986). These processes however need to use the expensive starting materials and to undergo several steps of reactions, so that the processes are rendered complicated disadvantageously.

In view of the aforementioned existing state of art, the present inventors have made intensive investigations and finally found that L-α-amino acids or D-α-amino acids are selectively produced when microorganisms belonging to Rhodococcus sp., Arthrobacter sp., Mycobacterium sp., Nocardiopsis sp. and Bacillus sp. and having the abilities of nitrile hydrolysis are caused to act on α-alkylideneaminonitrile compounds. The present invention has been completed on the basis of this finding and makes it the object to provide a process for the direct production of optically active amino acids such as L-α-amino acids and D-α-amino acids from α-aminonitrile compounds or derivatives thereof by making use of microorganisms selected from specific genera and having nitrile-hydrolyzing abilities.

SUMMARY OF THE INVENTION

The process of the present invention comprises causing a microorganism belonging to Rhodococcus sp., Arthrobacter sp., Mycobacterium sp. Nocardiopsis sp. or Bacillus sp. and having nitrile-hydrolyzing activity to act on one or more α-aminonitrile compounds represented by the following general formula (I):

and/or the following general formula (II):

at a pH in the range of 8–12 and/or in the presence of an aldehyde, or on one or more α-(N-alkylideneamino)nitrile or α-(N-phenylideneamino)nitrile compounds represented by the following general formula (III):

and/or the following general formula (IV):

to convert the compound or compounds to optically active amino acids such as L-α-amino acids and D-α-amino acids, R and R' in the above formulae being individually an alkyl group, substituted alkyl group, phenyl group, substituted phenyl group, imidazolyl group, substituted imidazolyl group, indolyl group, substituted indolyl group, furyl group, substituted furyl group, pyridyl group, substituted pyridyl group, thiazolyl group or substituted thiazolyl group, and R and R' may be the same or different groups.

DETAILED DESCRIPTION OF THE PREFERRED EMBODIMENTS OF THE INVENTION

The microorganisms useful in the practice of the present invention are, as described above, those selected from the group belonging to Rhodococcus sp., Mycobacterium sp., Arthrobacter sp., Nocardiopsis sp. and Bacillus sp. and having nitrile-hydrolyzing abilities and may be illustrated as in the following Table 1.

These microorganisms have been deposited to Fermentation Research Institute of the Agency of Industrial Science and Technology under the Budapest Treaty with Accession Numbers given in Table 1.

In the original application, Rhodococcus sp. PC-29, PA-34, AB-16 and BA-1 were deposited to the Institute under the mycological names of Nocardia sp. PC-29, PA-34, AB-16 and BA-1, while Arthrobacter sp. PA-15 and PC-3 were deposited under the mycological names of Corynebacterium sp. PA-15 and PC-3. However, according to the recent alteration of their classification, it has been found that the formers belong to Rhodococcus sp., while the latters to Arthrobacter sp. so that only the mycological names are modified.

The mycological properties of the above-described microorganisms are illustrated in Table 2.

TABLE 2

| Strain | Rhodococcus sp. | | | | Mycobacterium sp. | Arthrobacter sp. | |
|---|---|---|---|---|---|---|---|
| Properties | PC-29 | PA-34 | AB-16 | BA-1 | AB-43 | PA-15 | PC-3 |
| Shape | sphere | rod | sphere | sphere | rod | rod | rod |
| Motility | no | no | no | no | no | no | no |
| Spore | no | no | no | no | no | no | no |
| Gram stain | + | + | + | + | + | + | + |
| Oxidase | − | − | − | − | − | − | (+) |
| Catalase | + | + | + | + | + | + | + |
| O-F test | − | − | − | − | − | − | − |
| Growth on sole carbon sources | | | | | | | |
| Inositol | + | (+) | − | − | | | |
| Maltose | − | + | (+) | + | | | |
| Mannitol | + | + | + | + | | | |
| Rhamnose | + | (+) | − | − | | | |
| Sorbitol | + | + | + | + | | | |
| m-hydroxybenzoic acid | + | − | − | − | | | |
| Sodium adipate | + | + | − | − | | | |
| Sodium benzoate | + | + | + | + | | | |
| Sodium citrate | + | + | + | + | | | |
| Sodium lactate | + | + | + | + | | | |
| Testosterone | + | + | − | − | | | |
| L-tyrosine | − | + | + | − | | | |
| Glycerol | + | + | + | + | | | |
| p-hydroxybenzoic acid | − | (+) | + | − | | | |
| Growth in 5% NaCl | + | (+) | (+) | + | | | |
| Growth at 10° C. | + | (+) | (+) | (+) | | | |
| ONPG | + | − | − | − | | | |
| Decomposition of: | | | | | | | |
| Adenine | + | − | + | − | | | |
| Tyrosine | − | + | + | − | | | |
| Urea | + | − | + | + | | | |

TABLE 1

| Strain | FERM-BP No. |
|---|---|
| Rhodococcus sp. PC-29 | 1561 |
| *Rhodococcus rhodochrous* PA-34 | 1559 |
| Rhodococcus sp. AB-16 | 1555 |
| Rhodococcus sp. BA-1 | 1557 |
| Mycobacterium sp. AB-43 | 1556 |
| Arthrobacter sp. PA-15 | 1558 |
| Arthrobacter sp. PC-3 | 1560 |
| Nocardiopsis sp. A10-12 | 2422 |
| Nocardiopsis sp. B9-47 | 2423 |
| Bacillus sp. B9-40 | 3992 |
| Bacillus sp. A9-1 | 3991 |

As illustrated in Table 2, the above microorganisms used in the present invention are all Gram-positive aerobic bacteria and hence do not grow at all in anaerobic conditions. They do not exhibit motility, catalases being positive, and they do not form heat-resistant spores. They show mycelial growth in the early stage of culture. Branching cells and cocci are also observed in older cultures. As to the utilization of sugar, they do not generate gas from sugar, and their acid-forming ability is weak so that when they are incubated in litmus milk, the milk will turn blue indicating alkaline.

Among the above-described microorganisms, Rhodococcus sp. PC-29 forms somewhat dry and wrinkled colonies on nutrient agar and shows markedly branched mycelial growth in the early stage of culture. It grows at 5°–32° C. but does not grow at 37° C.

On the other hand, Rhodococcus sp. PA-34, AB-16 and BA-1 do not grow at 5°–10° C. but grow at 37°–42° C. They show mycelial growth in the early stage of culture and in older cultures shorter rods or cocci are formed.

The chemical analysis of the cells of these microorganisms has proved that they contain mycolic acid, the diamino acid in the walls being Meso DAP, and the fatty acid is composed of a saturated and/or unsaturated straight chain fatty acid and 10-methylstearic acid.

Mycobacterium sp. AB-43 is positive in acid-fast stain and does not grow at 45° C., forming viscous yellow-orange colonies.

Isolate AC-B-43

Mycolic acids are present. Cell wall diamino acid is meso-DAP. Fatty acid profile shows the presence of saturated straight chain acids (e.g. hexadecanoic acid $C_{16:0}$) unsaturated straight chain acids (e.g. octadecenoic acid, $C_{18:1}$) and branched acids where the branch occurs mid-chain (tuberculostearic acid) not the iso or anteiso branched acids (e.g. $iC_{15:0}$ or $aiC_{15:0}$ etc).

Arthrobacter sp. PA-15 and PC-3 are Gram-positive rods and their shapes are rather irregular. In older cultures, they form granules in the cells and exhibit a negative Gram stain, and shorter rods or cocci are formed The strains grow at 5°–10° C., but do not grow at 45° C. or higher. The colonies on nutrient agar are yellow-green and creamy, and have strong abilities of hydrolyzing both gelatin and starch but no ability of decomposing cellulose.

The chemical analysis of the cells of these microorganisms has confirmed that they do not contain mycolic acid, the diamino acid in the cell walls being lysine, and the fatty acid is a branched iso- and/or anteiso-fatty acid.

The above-described microorganisms are identified according to Bergey's Manual of Systematic Bacteriology, in view of the properties shown in Table 2 and as described above.

Further, the mycological and chemical properties of the above Nocardiopsis sp. are illustrated hereunder. The identification of the Nocardiopsis sp. is carried out primarily according to the method described in International Journal of Systematic Bacteriology 16, 313–340, 1966 by Shirling, E. B. and Gottlieb, D.

Nocardiopsis sp. A10-12:

1. Morphogenesis

Strain A10-12 is seen to extend a well branched, mesh-like substrate mycerium under an optical microscope. The aerial mycerium extended from the substrate mycerium exhibits the form of rectiflexibiles or retinaculiaperti, grows often in zigzags, and undergo fragmentation into rod cells in accordance with the lapse of culture time. Particular organs such as verticils, sclerotium and sporangium are not observed. The mature spores commonly comprise 10 or more chained spores, having sizes of approx. 0.5–0.8× 1.0–2.0 microns and smooth surfaces. The motility of the spores are not observed.

2. Growth state on various culture media:

The description of color tone is based on "Standard of Color" 1951 by Japan Color Research Institute, while the symbols and color tone given in [ ] are on "Color Harmony Manual" by Container Corporation of America.

1) Calcium malate agar medium (cultured at 27° C.):

Its growth is so slow that a colorless colony is formed 2 weeks after inoculation. In the 3rd week, a white aerial mycerium is evolved faintly on the light yellow [2ca, Lt Ivory] colony and no soluble pigment is observed.

2) Glucose-nitrate agar medium (cultured at 27° C.):

A brown-white [3ca, Shell] aerial mycerium is evolved on a light yellow-brown [2ec, Biscuit] colony and no soluble pigment is found.

3) Glucose-asparagine agar medium (cultured at 27° C.):

A white aerial mycerium is evolved slightly on a colorless colony and no soluble pigment is observed.

4) Starch-synthetic agar medium (cultured at 27° C.):

A white aerial mycerium is evolved thinly on a colorless to light yellow [2ca, Lt Ivory] colony, producing no solble pigment observable.

5) Sucrose-nitrate agar medium (cultured at 27° C.):

A brown-gray [2ba, Pearl] powdery aerial mycerium is evolved in plenty on a light yellow-brown [2ca-2gc, Lt Ivory-Bamboo] colony, no soluble pigment being recognized.

6) Yeast-malt agar medium (cultured at 27° C.):

A white aerial mycerium is evolved on a light yellow-brown [2ic, Honey Gold] colony, giving no soluble pigment observable.

7) Oatmeal agar medium (ISP3) (cultured at 27° C.):

A white aerial mycerium is evolved on a light yellow [2gc, Bamboo] colony and no soluble pigment is observed.

8) Starch inorganic salt agar medium (ISP4) (cultured at 27° C.):

A white to light yellow [2ca, Lt Ivory] aerial mycerium is evolved on a light yellow [2ea-2gc, Lt Wheat-Bamboo] colony and no soluble pigment is recognized.

9) Glycerol-asparagine agar medium (ISP5) (cultured at 27° C.):

A white aerial mycerium is evolved on a light yellow [2gc, Bamboo] colony, giving no soluble pigment observable.

10) Tyrosine agar medium (ISP7) (cultured at 27° C.):

A white to yellowish gray [2ec, Biscuit] aerial mycerium is evolved on a light yellow [2ea-2gc, Lt Wheat-Bamboo] colony and no soluble pigment is recognized.

11) Nutrient agar medium (cultured at 27° C.):

A white aerial mycerium is evolved abundantly on a light yellow [2ca, Lt Ivory] colony, producing no soluble pigment observable.

Physiological properties:

1) Growth temperature range:

As a result of cultivation at temperatures of 10° C., 20° C., 25° C., 31° C., 36° C., 40° C., 45° C. and 50° C. on a yeast extract-starch agar medium, strain A10-12 grows at temperatures from 10° C. to 36° C., but does not grow at 40° C., 45° C. and 50° C. The optimum growth temperature is ssumed to be approximately in the range between 25° C. and 31° C.

2) Liquefaction of gelatin (15% simple gelatin: cultured at 20° C. glucose-peptone-gelatin: cultured at 27° C.):

No liquefaction is observed in either of the media.

3) Hydrolysis of starch (starch inorganic salt agar medium: cultured at 27° C.):

Hydrolysis is observed slightly about 14 days after cultivation, and its action is rather weak.

4) Coagulation and peptonization of nonfat milk (nonfat milk: cultured at 37° C.):

Coagulation begins on about the 10th day after cultivation and is almost completed on about the 21st day. Peptonization begins on about the 14th day and is practically completed on the 21st day. The action is rather weak.

5) Utilization of calcium malate (calcium malate agar medium: cultured at 27° C.):

No dissolution of calcium malate is observed.

6) Reduction reaction of nitrate (peptone water containing 1.0% sodium nitrate ISP8: cultured at 27° C.):

possitive

7) Decomposition of cellulose (cultured at 27° C.): negative

8) Formation of melanin-like pigment (trypton-yeast-broth ISP1; peptone-yeast-iron agar medium ISP6; tyrosine agar medium ISP7: all cultured at 27° C.):

In all of the media, no formation of melanin-like pigment is observed.

9) Assimilation of carbon source (Pridham-Gottlieb agar medium ISP9: cultured at 27° C.):

The microorganism grows well by assimilating D-glucose, D-xylose, D-fructose, L-arabinose, D-mannitol and L-rhamnose. It also assimilates sucrose. Inositol does not appear to be assimilated, and raffinose can not be assimilated.

4. Cell wall components:

According to the method of the text of Lechevalier, M. P. and Lechevalier, H. A., Actinomycete Taxonomy Workshop, Soc. Ind. Microbiol. Aug. 13, 1978, the type of the cell walls of the whole cell is investigated and found to be the type III. The investigation has also clarified that the type of the sugar component in the whole cell is the type C in which only ribose is detected, and that the acyl type of muramic acid is the acetyl type.

The above properties are summarized as follows: with strain A-10, its substrate mycerium branches well on an agar medium and extends in a mesh-like state; in its early culture, an aerial mycerium is seen to grow in zigzags and its fragmentation is observed with the progress of its growth; the aerial mycerium grows in a rectiflexibiles or retinaculiaperti manner; and the spore has a size of 0.5–0.8×1.0–2.0 microns, 10 or more spores being commonly chained together, and the surface is smooth.

On all of the agar media, no particular organs such as sporangium, verticils and sclerotium are observed. Strain A10-12 evolves a white aerial mycerium on a light yellow-brown colony in each of the agar media, producing no soluble pigment observable.

With strain A10-12, the reducing properties of nitrate, the coagulation of milk, the peptonization of milk and the utilization of calcium malate are positive, whereas the hydrolysis of starch, the liquefaction of gelatin, the decomposition of cellulose and the production of melanin-like pigments (ISP1, ISP6 and ISP7) are negative. This strain is a mesophilic actinomycete, giving a salt resistance of 7.5–10%.

The type of cell wall using the whole cell of strain A10-12 is the type III, the type of sugar component being the type C, the acyl type of muramic acid being the acetyl type.

These properties have been referred to Bergey's Manual of Determinative Bacteriology (8th ed.) and "Hosenkin no Dotei Jikken-ho (Identifying Procedure on Actinomycetales)", The Society for Actinomycetales Japan, 1985, with the result that A10-12 sp. presumably belongs to any one of the species, Actinomadura, Excellospora, Actinosynnema and Nocardiopsis in view of the fact that the type of the cell walls is the type III and the strain comprises 20 or more chained spores. However, A10-12 is different from Actinomadura and Excellospora sp. in that the cell walls do not contain madurose and from Actinosynnema sp. in that no motile cells are formed in the aerial mycerium.

It seems reasonable to consider that strain A10-12 belongs to the J. Meyer's proposing Nocardiopsis sp. (Nocardiopsis, a new genus of the order Actinomycetes, Int. J. Syst. Bacteriol., 26 (4), 487–493, 1976) in view of the fact that characteristically (1) it forms an aerial mycerium, comprising 10 or more chained spores; (2) the aerial mycerium grows in zigzags and undergoes fragmentation with the passage of time; (3) the cell wall type is the type III; (4) the sugar contained in the cell walls is only ribose and hence belongs to the type C; (5) a white to yellowish gray aerial mycerium grows on a light yellow-brown colony.

It has been known that the Nocardiopsis sp. includes such "species" as *N. alba, N. atra, N. coeruleofusca, N. flava, N. longispora, N. mutabilis, N. syringae, N. dassonvillei, N. antarticus, N. trehalosei, N. africane* and *N. streptosporus*. strain A10-12 is however assumed to be probably a species similar to *N. dassonvilei* in the assimilative nature of carbon source and also in that only ribose is detected as the sugar component in the cell.

In consequence, strain A10-12 is concluded to be an actinomycete belonging to Nocardiopsis sp. from its morphological and physiological characteristics and from the characteristics of its cell wall components.

Strain B9-47:

1. Morphogenesis:

Strain B9-47 is seen to extend a well branched, mesh-like substrate mycerium under an optical microscope. The aerial mycerium extended from the substrate mycerium exhibits the form of rectiflexibiles or retinaculiaperti, grows often in zigzags, and undergoes fragmentation into rod cells in accordance with the lapse of culture time. No particular organs such as verticils, sclerotium and sporangium are observed. The mature spores commonly comprise 10 or more chained spores, having sizes of approx. 0.5–0.8× 1.0–2.0 microns and smooth surfaces. The motility of the spores are not observed.

2. Growth state on various culture media:

The description of color tone is based on "Standard of Color" 1951 by Japan Color Research Institute, while the symbols and color tones given in [ ] are on "Color Harmony Manual" by Container Corporation of America.

1) Calcium malate agar medium (cultured at 27° C.):

A white aerial mycerium is evolved on a colorless colony, giving no soluble pigment observable.

2) Glucose-nitrate agar medium (cultured at 27° C.):

A white aerial mycerium is evolved on a light yellow-brown [2ec, Biscuit] colony, and the soluble pigment produced assumes a brownish color.

3) Glucose-asparagine agar medium (cultured at 27° C.):

Almost no growth is observed.

4) Starch-synthetic agar medium (caltured at 27° C.):

A white aerial mycerium is evolved on a light yellow-brown [2gc, Bamboo] colony, and the soluble pigment produced assumes a yellowish color.

5) Sucrose-nitrate agar medium (cultured at 27° C.):

A white aerial mycerium is evolved on a colorless colony and no soluble pigment is found.

6) Yeast-malt agar medium (cultured at 27° C.):

A white aerial mycerium is evolved on a colorless colony, giving no soluble pigment recognizable.

7) Oatmeal agar medium (ISP3) (cultured at 27° C.):

A white aerial mycerium is evolved on a colorless colony, giving no soluble pigment observable.

8) Starch inorganic salt agar medium (ISP4) (cultured at 27° C.):

A yellow-orange [3ca, Shell] aerial mycerium is evolved on a light yellow-brown [2ea, Lt Wheat] colony, and no soluble pigment is observed.

9) Glycerol-asparagine agar medium (ISP5) (cultured at 27° C.):

A white aerial mycerium is evolved on a light yellow [2gc, Bamboo] colony, producing no soluble pigment observable.

10) Tyrosine agar medium (ISP7) (cultured at 27° C.):

A white aerial mycerium is evolved on a light yellow [3ec, Bisque] colony, producing a reddish soluble pigment observable.

11) Nutrient agar medium (cultured at 27° C.):

A white aerial mycerium is evolved abundantly on a light yellow [3ec, Bisque] colony and no production of soluble pigment is seen.

3. Physiological properties:

1) Growth temperature range:

As a result of cultivation at temperatures of 10° C., 20° C., 25° C., 31° C., 36° C., 40° C., 45° C . and 50° C. on a yeast extract-starch agar medium, B9-47 sp. grows at temperatures from 10° C. to 36° C., but does not grow at 40° C., 45° C. and 50° C. The optimum growth temperature is assumed to be approximately in the range between 25° C. and 31° C.

2) Liquefaction of gelatin (15% simple gelatin: cultured at 20° C., glucose-peptone-gelatin: cultured at 27° C.):

Liquefaction is seen in both of the media and its actions are moderate.

3) Hydrolysis of starch (starch inorganic salt agar medium: cultured at 27° C.):

Hydrolysis is observed slightly about 14 days after cultivation and its action is rather weak.

4) Coagulation and peptonization of nonfat milk (nonfat milk: cultured at 37° C.):

Coagulation begins on about the 10th day after cultivation and is completed on about the 21st day. Peptonization begins on about the 14th day and is practically completed on the 21st day. The action is rather weak.

5) Utilization of calcium malate (calcium malate agar medium: cultured at 27° C.):

No dissolution of calcium malate is observed.

6) Reduction reaction of nitrate (peptone water containing 1.0% sodium nitrate ISP8: cultured at 27° C.):

possitive

7) Decomposition of cellulose (cultured at 27° C.):

negative

8) Formation of melanin-like pigment (trypton-yeast-broth ISP1, peptone-yeast-iron agar medium ISP6, tyrosine agar medium ISP7: all cultured at 27° C.):

In all of the media, no formation of melanin-like pigment is observed.

9) Assimilation of carbon source (Pridham-Gottlieb agar medium ISP9: cultured at 27° C.):

The microorganism grows well by assimilating D-glucose, D-xylose, D-fructose, L-arabinose and D-mannitol. It does not assimilate inositol, sucrose, L-rhamnose and raffinose.

4. Cell wall components:

According to the method of the text of Lechevalier, M. P. and Lechevalier, H. A., Actinomycete Taxonomy Workshop, Soc. Ind. Microbiol. Aug. 13, 1978, the type of the cell walls of the whole cell is investigated and found to be the type III. The investigation has also clarified that the type of sugar component in the whole cell is the type C in which ribose and some glucose are detected, and that the acyl type of muramic acid is the acetyl type.

The above properties are summarized as follows: with strain B9-47, its substrate mycerium branches well on an agar medium and extends in a mesh-like state; in its early culture, an aerial mycerium is seen to grow in zigzags and its fragmentation is observed with the progress of its growth; the aerial mycerium grows in a rectiflexibiles or retinaculiaperti manner; and the spore has a size of 0.5–0.8×1.0–2.0 microns, 20 or more spores being chained together, and has a smooth surface.

On all of the agar media, no particular organs such as sporangium, verticils and sclerotium are observed. Strain B9-47 evolves a white aerial mycerium on a light yellow to light yellow-brown colony in each of the agar media, producing a reddish to brownish soluble pigment observable.

With strain B9-47, the reducing properties of nitrate, the coagulation of milk, the peptonization of milk and the liquefaction of gelatin are positive, whereas the utilization of calcium malate, the hydrolysis of starch, the decomposition of cellulose and the production of melanin-like pigments (ISP1, ISP6 and ISP7) are negative. This strain is a mesophilic actinomycete, giving a salt resistance of 7.5–10%.

The type of cell wall using the whole cell of strain B9-47 is the type III, the type of sugar component being the type C, the acyl type of muramic acid being the acetyl type.

These properties have been referred to Bergey's Manual of Determinative Bacteriology (8th ed.) and "Hosenkin no Dotei Jikken-ho" (Identifying Procedure on Actinomycetales), The Society for Actinomycetales Japan, 1985, with the result that strain B9-47 presumably belongs to any one of the species, Actinomadura, Excellospora, Actinosynnema and Nocardiopsis in view of the fact that the type of the cell walls is the type III and the strain comprises 20 or more chained spores. However, strain B9-47 is different from Actinomadura and Excellospora sp. in that the cell walls do not contain madurose and also from Actinosynnema sp. in that motile cells are formed in the aerial mycerium.

It seems reasonable to consider that strain B9-47 belongs to the J. Meyer's proposing Nocardiopsis sp. (Nocardiopsis, a new genus of the order Actinomycetes, Int. J. Syst. Bacteriol., 26 (4), 487–493, 1976) in view of the fact that characteristically (1) the aerial mycerium grows in zigzags and undergoes fragmentation with the passage of time; (2) the cell wall type is the type III; (3) the sugar contained in the cell walls is only ribose.

It has been known that the Nocardiopsis sp. includes such "species" as *N. alba, N. atra, N. coeruleofusca, N. flava, N. longispora, N. mutabilis, N. sryingae, N. dassonvillei, N. antarticus, N. trehalosei, N. africane* and *N. streptosporus.* strain B9-47 is however assumed to be probably a species similar to any one of *N. dassonvilei, N. antarticus* and *N. trehalosei* in the assimilative nature of carbon source and also in that ribose and some glucose are detected as the sugar component in the cell.

In consequence, strain B9-47 is concluded to be an actinomycete belonging to Nocardiopsis sp. from its morphological and physiological characteristics and from the characteristics of its cell wall components.

Then, the mycological and chemical properties of the strains of Bacillus sp. are shown in Table 3.

TABLE 3

| Stain Properties | Bacillus Sp. B9-40 | Bacillus sp. A9-1 |
|---|---|---|
| Shape | rod | rod |
| Gram stain | + | unstable |
| Spore | + | + |
| Flagellum | + | + |
| Color of colony | yellowish brown | yellowish brown |
| Growth temperature | 37° C.  + | 37° C.  + |
|  | 41° C.  − | 41° C.  − |
|  | 45° C.  − | 45° C.  − |
|  | 50° C.  − |  |

TABLE 3-continued

| Stain Properties | Bacillus Sp. B9-40 | Bacillus sp. A9-1 |
| --- | --- | --- |
| Catalase | + | + |
| Oxidase | + | + |
| OF test | − | not grow at 25 & 30 |
| Test conditions | 30° C., pH 7.2 | 30° C., pH 9 |
| Shape of spore | oval or cylinder | oval or cylinder |
| Sporangium formation | − | + |
| Spore location | center to end | center to end |
| Intracellular grain | − | − |
| Anaerobic growth | − | + |
| Growth in 5% NaCl | + | + |
| Growth in 7% NaCl | + | + |
| Growth in 10% NaCl | + | + |
| Growth in pH 5.7 broth | − | − |
| Acid formation from glucose | − | − |
| Gas formation from glucose | − | − |
| VP reaction | − | − |
| Yolk reaction | − | not measured |
| Casein decomposition | + | − |
| Gelatin decomposition | + | − |
| Tyrosine decomposition | − | − |
| Starch hydrolysis | + | − |
| Reduction of nitrate | − | + |
| Utilization of citric acid | (+) | + |
| Arginine dihydrolase | − | not measured |
| -Galactosidase activity | − | + |
| Urease test | − | − |
| Growth at pH 7.2 | not tested | − |
| Tween 80 hydrolysis | not tested | + |

(+): weak positive reaction

When the mycological and chemical properties of the above strains are referred to Bergey's Manual of Determinative Bacteriology (8th ed.), these strains are identified as strains belonging to Bacillus sp.

In the present invention, the α-aminonitrile compounds represented by the foregoing general formulae (I) and (II), the substrates for producing optically active amino acids by utilizing the aforesaid microorganisms, may be synthesized with ease according to the synthetic process of α-aminonitriles, i.e., the first stage reaction in the Strecker process [for example, J. Ferment. Technol., 49 1011 (1971) or Chem. Lett., 687 (1987)], or to the process disclosed in Org. Syn. Col. Vol. I, p. 21 and III, p. 84.

On the other hand, the α-(N-alkylideneamino)nitrile compounds represented by the general formulae (III) and (IV), which are another substrate, may be obtained in such a way that as soon as the aldehydes used as a raw material are confirmed to disappear by the analysis using gas chromatography, etc. in the synthesis of α-aminonitrile compounds, which is the first stage reaction in the Strecker process, inorganic salts are separated out by such a procedure as filtration or extraction and the resulting solutions are concentrated. The crude products may in some cases contain, as impurities, α-aminonitriles, which are the partial hydrolysis products of α-(N-alkylideneamino)nitrile compounds represented by the foregoing general formulae (III) and (IV), and aldehydes used as a raw material for the synthesis. After these impurities have been removed by such a procedure as fractional distillation, the resulting products are used as the substrate. However, the crude products containing the impurities may also be used as the substrate.

R and R' in the general formulae (I) (II) (III) and (IV) representing α-aminonitrile compounds and derivatives thereof, i.e., α-(N-alkylideneamino)nitrile compounds, are individually an alkyl group, substituted alkyl group, phenyl group, substituted phenyl group, imidazolyl group, substituted imidazolyl group, indolyl group, substituted indolyl group, furyl group, substituted furyl group, pyridyl group, substituted pyridyl group, thiazolyl group or substituted thiazolyl group. No particular limitations are imposed on the substitutents in the substituted alkyl group, substituted phenyl group, substituted imidazolyl group, substituted indolyl group, substituted furyl group, substituted pyridyl group and substituted thiazolyl group, among these Rs. However, as the preferred substituents may be mentioned hydroxyl, methoxyl, mercapto, methylmercapto, amino, halogeno, carboxyl, carboxamide, phenyl, hydroxyphenyl and guanyl by way of example.

Further, where the compounds of the general formulae (III) and (IV) are used as a substrate, use of the compound having the same groups for both R and R' as a raw material may lead to the formation of an optically active amino acid, e.g. an L-α-amino acid, while use of the compound having different groups for R and R' as a raw material can result in the formation of a mixture of two optically active amino acids, e.g. two L-α-amino acids.

It goes without saying that the aforesaid nitrile compounds and derivatives thereof used as the raw material may be used as a mixture of two or more of them without any inconvenience.

Illustrative examples of the above-described α-aminonitrile compound may include 2-aminopropanenitrile, 2-amino-butanenitrile, 2-amino-3-methylbutanenitrile, 2-amino-4-methyl-pentanenitrile, 2-amino-3-methylpentanenitrile, 2-amino-3-hydroxypropanenitrile, 2-amino-3-hydroxybutanenitrile, 2-amino-5-guanidinopentanenitrile, 2-amino-3-mercaptopropanenitrile, 2,7-diamino-4,5-dithiaoctanenitrile, 2-amino-4-methylthiobutanenitrile, 2-amino-3-phenylpropanenitrile, 3-(4-hydroxyphenyl)propanenitrile, 3-amino-3-cyanopropanoic acid, 4-amino-4-cyanobutanoic acid, 3-amino-3-cyanopropanamide, 4-amino-4-cyanobutanamide, 2,6-diaminohexanenitrile, 2,6-diamino-5-hydroxyhexanenitrile, 2-amino-3-(3-indolyl)propanenitrile, 2-amino-3-(4-imidazolyl)propanenitrile, 2-cyanopyrrolidine, 2-cyano-4-hydroxypyrrolidine and 2-amino-2-phenylethanenitrile.

On the other hand, as the α-(N-alkylideneamino)nitrile compounds may be mentioned the Schiff base compounds of the α-aminonitrile compounds as illustrated above with the aldehydes which are the raw material for the synthesis of the α-aminonitriles.

In the present invention, where the α-aminonitrile compound is used as a substrate, the substrate is brought into contact with a microorganism at a pH in the range of 8–12 or else it is brought into contact with a microorganism in the presence of an aldehyde. As the aldehyde used for this purpose, it is possible to use the aldehyde, which is used as a raw material in the synthesis of the aminonitrile compounds represented by the general formula (I) or (II) illustrated above. In this case, using a single aldehyde a single optically active amino acid is obtained, whereas use of a different aldehyde may result in the formation of a mixture of different optically active amino acids.

In the present invention, in order to produce an optically active amino acid by causing each of the above-described microorganisms, which belong to Rhodococcus sp., Mycobacterium sp., Arthrobacter sp., Nocardiopsis sp. and Bacillus sp. and have nitrile-hydrolyzing activities, to act on the aforementioned nitrile compound or derivative thereof used as a raw material (hereinafter abbreviated as "the raw nitrile"), it is advisable to use any one of the following processes (a) to (c).

Specifically, it is possible to employ (a) a process comprising incubating a microorganism in a medium containing a nitrile compound such as propionitrile to obtain a cell mass and bringing the thus-proliferated cell mass into contact with the raw nitrile or the raw nitrile plus an aldehyde to react them with each other, (b) a process comprising incubating a microorganism in advance, bringing the thus-proliferated cell mass into contact with a nitrile compound such as propionitrile, and adding to the resulting cell mass the raw nitrile or the raw nitrile plus an aldehyde to react them with each other, or (c) a process comprising incubating a microorganism in advance, and bringing the thus-proliferated cell mass into direct contact with the raw nitrile or the raw nitrile plus an aldehyde to react them with each other.

In these reaction processes, it is also feasible to use destructed products of proliferated cells, dried cells, enzyme preparations such as cell free extract and purified nitrile-hydrolyzing enzymes, or cells and enzyme preparations immobilized according to conventional procedures.

The nitrile compounds useful in the practice of the processes (a) and (b) may embrace acetonitrile, n-butyronitrile, n-capronitrile, methacrylonitrile, isobutyronitrile, glutaronitrile, triacrylonitrile, crotononitrile, lactonitrile, succinonitrile, acrylonitrile, benzonitrile, phenylacetonitrile, etc. as well as propionitrile.

In the foregoing process (a), the preculture of each of the above-described microorganisms is inoculated to a medium which has been added with carbon sources such as glucose, sucrose, molasses and starch-hydrolyzate, acetic acid and other utilizable carbon sources in addition to the nitrile compound, and further with a nitrogen source such as ammonium chloride, ammonium sulfate, ammonium phosphate, ammonium nitrate, urea, aqueous ammonia, sodium nitrate, and amino acids and other utilizable organic nitrogen compounds, inorganic salts such as calcium phosphate, sodium phosphate, magnesium sulfate, manganese sulfate, iron (II) sulfate, iron (III) chloride, calcium chloride and manganese chloride, salts of boric acid, salts of copper, zinc, etc., what is called micronutrients, and optionally growth-promoting materials such as vitamins, yeast extracts and corn steep liquor. The preculture is incubated therein under aerobic conditions to cause the cells to proliferate. The raw nitrile or the raw nitrile plus an aldehyde is added to the thus-obtained cultured broth, a suspension of the cells separated from the cell-culture or enzyme preparations to react them with each other.

When an α-aminonitrile compound is reacted in the absence of the aldehyde, the reaction is carried out at a pH in the range of 8–12, whereas otherwise it is effected at a pH in the range of 4–13, preferably 8–12, for 1–6 days in both cases. If an α-aminonitrile compound is reacted at a pH outside the range of 8–12 in the absence of an aldehyde, an α-amino acid rich in L-configuration or an α-amino acid rich in D-configuration is formed, which is however low in optical purity and hence has no practical use. In this reaction, a variety of buffer solutions may be used. Of these, ammoniacal buffer solutions are preferred, including, for example, a mixture of aqueous ammonia and aqueous ammonium chloride solution, a mixture of aqueous ammonia and aqueous ammonium sulfate solution, a mixture of aqueous ammonia and aqueous ammonium phosphate solution, and a mixture of aqueous ammonia and aqueous ammonium acetate solution. Further, as the alkali for use to control pH, aqueous ammonia is preferred.

The reaction temperature should preferably fall within the range of 20°–70° C. Further, the above-described carbon source, nitrogen source and other components used to proliferate the cells may be added properly to the reaction system to maintain and enhance the cell concentration or the cell's ability of nitrile hydrolysis. In the feeding of the raw nitrile, any one of the following methods may be employed: a method of adding at the time of reaction initiation, a method of intermittent addition or a method of continuous addition.

In the foregoing process (b), the nitrile compound is not added during incubation and proliferation of the cell mass as in the foregoing process (a), but is added after the cell mass has been proliferated so that the ability of nitrile hydrolysis of the mass of the microorganism is activated. Then, the cell mass is reacted with the raw nitrile or the raw nitrile plus an aldehyde to produce an optically active amino acid.

In the foregoing process (c), as soon as the cell mass has been proliferated as in the process (b), the raw nitrile or the raw nitrile plus an aldehyde is added thereto for effecting reaction to produce an optically active amino acid.

In either of the processes (b) and (c), it is possible to employ the same incubation conditions, reaction conditions and separation and collection procedures of the produced optically active amino acid as those used in the process (a).

As regards the amount of an aldehyde to be used where the reaction is conducted in the presence of the aldehyde, it is preferable to use 0.1–10 mols, particularly 0.5–3 mols of the aldehyde per mol of an α-aminonitrile compound.

The optically active amino acids formed by the above-described reactions are isolated by the use of well-known procedures such as phase separation, filtration, extraction and column chromatography.

The optically active amino acids obtained according to the present invention as described above can find their applications in a variety of fields including those of foods, feeds, pharmaceuticals and cosmetics.

As has been illustrated above, the present invention permits the direct and selective production of optically active amino acids from racemic α-aminonitrile compounds or derivatives thereof by making use of microorganisms. Thus, the present invention is useful in the production of optically active amino acids such as L-α-amino acids and D-α-amino acids which are utilized in a variety of fields as described above.

The present invention will be illustrated more specifically by reference to the following examples. However, it should not be construed that the present invention is limited to or by the examples.

EXAMPLES

Example 1

(1) Preparation of medium:

A medium (100 ml) of the following composition was placed in a 500-ml flask, which was then sterilized at 120° C. for minutes in an autoclave. To the medium was added 1 ml of propionitrile having been sterilized by means of a 0.2-Millipore Filter. The medium for the preparation of cell mass was thus obtained.

Medium composition:

| | |
|---|---|
| glucose | 10 g/l |
| yeast extract | 0.1 g/l |
| $Na_2HPO_4$ $12H_2O$ | 2.5 g/l |
| $KH_2PO_4$ | 2.0 g/l |
| $MgSO_4$ $7H_2O$ | 0.5 g/l |
| $FeSO_4$ $7H_2O$ | 0.03 g/l |
| $CaCl_2$ $2H_2O$ | 0.06 g/l |
| pH | 7.2 |

Strains for use:

| Name of strain | FERM-BP No. |
| --- | --- |
| Rhodococcus sp. PC-29 | 1561 |
| *Rhodococcus rhodochrous* PA-34 | 1559 |
| Rhodococcus sp. AB-16 | 1555 |
| Rhodococcus sp. BA-1 | 1557 |
| Mycobacterium sp. AB-43 | 1556 |
| Arthrobacter sp. PA-15 | 1558 |
| Arthrobacter sp. PC-3 | 1560 |

(2) Incubation and proliferation of cell mass:

To the medium prepared as described above were inoculated 3 loopfuls of each of the five strains given in Table 4. The resultant medium was incubated under oscillation at 140 rpm at a temperature of 30° C. for 48 hours.

The cell mass obtained by the incubation was isolated by centrifugation, washed once with a 0.1M $NH_4Cl$—$NH_3$ buffer solution (pH 10), and thereafter resuspended in a 0.1M $NH_4Cl$—$NH_3$ buffer solution so as to adjust the optical density (OD) at 40.

(3) Reaction:

Into a test tube with an inner diameter of 24 mm was admitted 5 ml of each of the cell suspensions obtained as described above. Then, 50 mg of DL-2-amino-2-phenylethanenitrile was added thereto and the test tube was stopcocked. The test tube was shaken at 300 rpm at a temperature of 30° C. for 48 hours.

After completion of the reaction, the reaction mixture was extracted twice with 5 ml of hexane, and the water phase thus-obtained was analyzed by high performance liquid chromatography (hereinafter simply abbreviated as HPLC).

The quantity of L-α-phenylglycine thus-formed was determined by means of an amino acid analyzer (manufactured by Beckman Co.: Type 7300). Its absolute configuration and optical purity were determined by HPLC using CHIRALPAK WH (product of Daicel Chemical Industries, Ltd.) as a column packing. The results are as shown in Table 4.

TABLE 4

| | L-α-phenylglycine | |
| --- | --- | --- |
| Strain | Amount (mg/ml) | Optical purity (% e.e.) |
| Rhodococcus sp. PC-29 | 0.4 | not less than 99 |
| *Rhodococcus rhodochrous* sp. PA-34 | 0.2 | ditto |
| Rhodococcus sp. AB-16 | 0.1 | ditto |
| Rhodococcus sp. BA-1 | 0.1 | ditto |
| Mycobacterium sp. AB-43 | 0.5 | ditto |

Example 2

In the same manner as in Example 1, a cell mass of Rhodococcus sp. PA-34 was prepared and collected, and then resuspended in a 0.1M $NH_4Cl$—$NH_3$ buffer solution so as to adjust the optical density (OD) at 40. Thereafter, 500 ml of the cell suspension thus-obtained was admitted in a 1.2-l fermenter, to which 4.9 g (50 mmol) of DL-2-amino-3-methylbutanenitrile was added. While maintaining the pH at 10.0+0.1 with 4N aqueous ammonia, the resulting suspension was submitted to reaction at a temperature of 30° C. and at 700 rpm agitation for 48 hours.

After completion of the reaction, the reaction mixture was centrifuged to obtain a supernatant, which was then filtered by means of a 0.45-μ Millipore Filter. The resulting water phase was analyzed by HPLC.

The accumulated concentration of L-valine was 0.5 mg/ml, while the optical purity thereof was 67% e.e. The quantity of L-valine was determined by HPLC using inertsil ODS (product of Gasukuro Koygoy Inc.) as a column packing. Its absolute configuration and optical purity were determined similarly by HPLC using CHIRALPAK WH (product of Daicel Chemical Industries, Ltd.).

Comparative Example 1

Reaction and analysis were conducted by using the same cell mass and in the same manner as described in Example 2 except that the pH was adjusted at 7.0+0.1 with 4N aqueous ammonia and 1N HCl in the procedure described in Example 2. As a consequence, the accumulated concentration of L-valine was found to be 3.5 mg/ml, while its optical purity was 32% e.e.

Comparative Example 2

A cell mass of Rhodococcus sp. PA-34 was prepared in the same manner as described in Example 1. After the mass had been collected by centrifugation, it was washed twice with a 0.1M $Na_2HPO_4$—$KH_2PO_4$ buffer solution (pH 7.0) and then resuspended in a 0.1M $Na_2HPO_4$-$KH_2PO_4$ buffer solution so as to adjust the optical density (OD) at 40. The resulting cell suspension was subjected to reaction and analysis in the same manner as described in Comparative Example 1. The results revealed that L-valine had an accumulated concentration of 4.3 mg/ml and an optical purity of 17% e.e.

Example 3

A cell mass of Rhodococcus sp. PA-34 was prepared in the same manner as in Example 1, and was resuspended in a 0.1M $NH_4Cl$—$NH_3$ buffer solution so as to adjust the optical density (OD) at 40. Then, 500 ml of the resulting cell suspension was admitted in a 1.2-l fermenter, to which 4.9 g (50 mmol) of DL-2-amino-3-methylbutanenitrile and 7.2 g (100 mmol) of isobutyraldehyde were added. They were reacted under stirring for 48 hours at a temperature of 30° C., at 700 rpm agitation, and at 0.2 vvm aeration, while maintaining the pH at 10.0+0.1 with 4N aqueous ammonia and 1N HCl.

After completion of the reaction, the reaction mixture was analyzed in the same manner as described in Example 2. As a result, it was found that the accumulated concentration of L-valine was 1.3 mg/ml, while its optical purity was 96% e.e.

Example 4

Using each of the microorganisms given in Table 5, a cell suspension was prepared in the same manner as described in Example 1. Then, 5 ml of the cell suspension was admitted in a test tube having an inner diameter of 24 mm, to which 49 mg of DL-2-amino-3-methylbutanenitrile and 72 mg of isobutyraldehyde were added. The test tube was stopcocked and the contents were reacted for 48 hours at a temperature of 30° C. under 300 rpm oscillation. The reaction mixture thus-obtained was treated and analyzed in the same manner as described in Example 2. The results are given in Table 5.

TABLE 5

| | L-valine | |
|---|---|---|
| Strain | Amount (mg/ml) | Optical purity (% e.e.) |
| Rhodococcus sp. PC-29 | 0.8 | 100 |
| Rhodococcus sp. AB-16 | 0.5 | 96 |
| Rhodococcus sp. BA-1 | 0.4 | 100 |
| Mycobacterium sp. AB-43 | 0.6 | 97 |

Example 5

Using each of the microorganisms given in Table 6, a cell suspension was prepared in the same manner as described in Example 1. Reaction was carried out according to the procedure described in Example 4 except for the addition of 50 μl of DL-2-aminopentanenitrile and 60 μl of n-butyraldehyde to 5 ml of the cell suspension. The L-norvaline thus-formed was analyzed by HPLC using Inertsil ODS and CHIRALPAK WE as column packings. The results are shown in Table 6.

TABLE 6

| | L-norvaline | |
|---|---|---|
| Strain | Amount (mg/ml) | Optical purity (% e.e.) |
| Mycobacterium sp. AB-43 | 3.4 | 92 |
| Rhodococcus rhodochrous PA-34 | 3.5 | 98 |

Example 6

Using each of the microorganisms given in Table 7, a cell suspension was prepared in the same manner as described in Example 1. Reaction was carried out following the procedure described in Example 4 except for the addition of 50 μl of DL-4-methyl-2-aminopentanenitrile and 60 μl of 3-methylbutyraldehyde to 5 ml of the cell suspension. The L-leucine thus-formed was analyzed in the same manner as described in Example 5. The results are shown in Table 7.

TABLE 7

| | L-leucine | |
|---|---|---|
| Strain | Amount (mg/ml) | Optical purity (% e.e.) |
| Mycobacterium sp. AB-43 | 1.4 | 97 |
| Rhodococcus rhodochrous PA-34 | 1.6 | 95 |

Example 7

Using each of the microorganisms given in Table 8, a cell suspension was prepared in the same manner as described in Example 1. Reaction was carried out following the procedure described in Example 4 except for the addition of 50 μl of DL-aminohexanenitrile and 60 μl of n-pentylaldehyde. The L-norleucine thus-formed was analyzed as described in Example 5. The results are shown in Table 8.

TABLE 8

| | L-norleucine | |
|---|---|---|
| Strain | Amount (mg/ml) | Optical purity (% e.e.) |
| Mycobacterium sp. AB-43 | 1.1 | 100 |
| Rhodococcus rhodochrous PA-34 | 1.3 | 100 |

Example 8

Three loopfuls of Arthrobacter sp. PA-15 strain were inoculated to 100 ml of an NBG medium in a 500-ml Sakaguchi flask [the NBG medium is a liquid medium prepared by adding deionized water to 10 g of "Lab-Lemco" powder (code L29: product of Oxoid Co., Ltd.), 10 g of Bacteriological peptone (code L37), 10 g of glucose and 5 g of sodium chloride to make the total volume 1,000 ml, adjusting the pH of the resulting liquid at 7.5 with 1N aqueous sodium hydroxide solution, and then sterilizing the liquid with heat at 120° C. for 15 minutes in an autoclave]. The cells were cultured under oscillation (150 times/minutes) at 30° C. for 48 hours. The cell mass formed by the incubation was collected and washed in the same manner as described in Example 1, and resuspended in a 0.1M $NH_4Cl$—$NH_3$ buffer solution so as to adjust the optical density (OD) at 40. The cell suspension was reacted with DL-2-amino-3-methylbutanenitrile in the presence of isobutyraldehyde in the same manner as described in Example 4. The accumulated concentration of L-valine was 0.3 mg/ml and its optical purity was 95% e.e.

Example 9

Reaction was carried out in the same manner as described in Example 4 except that 50 μl of DL-2-aminopentanenitrile and 60 μl of n-butyraldehyde were added to 5 ml of each of the cell suspensions prepared according to the procedure given in Example 8. The L-norvaline thus-formed was analyzed as described in Example 5. The results are shown in Table 9.

TABLE 9

| | L-norvaline | |
|---|---|---|
| Strain | Amount (mg/ml) | Optical purity (% e.e.) |
| Rhodococcus sp. BA-1 | 2.7 | 100 |
| Arthrobacter sp. PA-15 | 2.7 | 84 |
| Arthrobacter sp. PC-3 | 2.8 | 82 |

Example 10

Reaction was carried out in the same manner as described in Example 3 except that 50 μl of DL-4-methyl-2-aminopentanenitrile and 60 μl of 3-methylbutyraldehyde were added to 5 ml of each of the cell suspensions prepared according to the procedure given in Example 8. The L-leucine thus-formed was analyzed as described in Example 5. The results are shown in Table 10.

TABLE 10

| | L-leucine | |
|---|---|---|
| Strain | Amount (mg/ml) | Optical purity (% e.e.) |
| Rhodococcus sp. BA-1 | 0.6 | 85 |
| Arthrobacter sp. PA-15 | 1.2 | 94 |
| Arthrobacter sp. PC-3 | 1.1 | 91 |

Example 11

Reaction was carried out in the same manner as described in Example 4 except that 50 μl of DL-2-aminohexanenitrile and 60 μl of n-pentylaldehyde were added to 5 ml of each of the cell suspensions prepared according to the procedure given in Example 8. The L-norleucine thus-formed was analyzed as described in Example 5. The results are shown in Table 11.

TABLE 11

| | L-leucine | |
|---|---|---|
| Strain | Amount (mg/ml) | Optical purity (% e.e.) |
| Arthrobacter sp. PA-15 | 0.7 | 100 |
| Arthrobacter sp. PC-3 | 0.7 | 100 |

Example 12

Cell suspensions of the strains given in Table 12 were prepared according to the procedure described in Example 1. In a test tube with an inner diameter of 24 mm was admitted 5 ml of each cell suspension, to which 100 μl of DL-3-methyl-2-(N-2-methylpropylideneamino)butanenitrile were added. The test tube was stopcocked, and the contents were incubated at 30° C. under oscillation at 300 rpm for 48 hours.

After completion of the reaction, the resulting reaction mixture was extracted twice with 5 ml of hexane. The remaining water phase was analyzed by HPLC as described in Example 2. The results are as shown in Table 12.

TABLE 12

| | L-valine | |
|---|---|---|
| Strain | Amount (mg/ml) | Optical purity (% e.e.) |
| Rhodococcus sp. PC-29 | 2.3 | 96 |
| Rhodococcus rhodochrous sp. PA-34 | 0.6 | 98 |
| Rhodococcus sp. AB-16 | 1.3 | 92 |
| Rhodococcus sp. BA-1 | 0.9 | 95 |
| Mycobacterium sp. AB-43 | 3.0 | 97 |
| Arthrobacter sp. PA-15 | 2.5 | 100 |
| Arthrobacter sp. PC-3 | 1.6 | 100 |

Example 13

The procedure described in Example 12 was followed except for the addition of 50 mg of DL-4-methyl-2-(N-3-methylbutylideneamino)pentanenitrile to 5 ml of the cell suspension of each strain given in Table 13; the cell suspension was prepared according to the procedure described in Example 1. (The produced L-leucine was analyzed as described in Example 5.) The results are shown in Table 13.

TABLE 13

| | L-leucine | |
|---|---|---|
| Strain | Amount (mg/ml) | Optical purity (% e.e.) |
| *Rhodococcus rhodochrous* sp. PA-34 | 2.5 | 93 |
| Mycobacterium sp. AB-43 | 0.6 | 83 |

Example 14

The procedure described in Example 12 was followed except for the addition of 50 μl of DL-2-(N-butylideneamino)pentanenitrile to 5 ml of the cell suspension of each strain given in Table 14, the cell suspension being prepared according to the procedure described in Example 1. The results are shown in Table 14.

TABLE 14

| | L-norvaline | |
|---|---|---|
| Strain | Amount (mg/ml) | Optical purity (% e.e.) |
| Rhodococcus sp. AB-16 | 2.6 | 90 |
| Mycobacterium sp. AB-43 | 2.4 | 66 |
| *Rhodococcus rhodochrous* sp. PA-34 | 2.1 | 90 |
| Rhodococcus sp. PC-29 | 1.5 | 60 |

Example 15

The procedure described in Example 12 was followed except for the addition of 50 μl of DL-2-(N-pentylideneamino)hexanenitrile to 5 ml of the cell suspension of each strain given in Table 15, the cell suspension being prepared according to the procedure described in Example 1. The results are shown in Table 15.

TABLE 15

| | L-norleucine | |
|---|---|---|
| Strain | Amount (mg/ml) | Optical purity (% e.e.) |
| Rhodococcus sp. AB-16 | 1.3 | 98 |
| Mycobacterium sp. AB-43 | 0.8 | 86 |
| *Rhodococcus rhodochrous* sp. PA-34 | 1.1 | 96 |
| Rhodococcus sp. PC-29 | 0.5 | 51 |

Example 16

A cell suspension of Rhodococcus sp. PA-34 was prepared according to the procedure described in Example 1 except that each of the nitrile compounds given in Table 16 was used in place of propionitrile. To 5 ml of the cell suspension was added 50 μl of DL-3-methyl-2-(N-2-methylpropylideneamino)butanenitrile. Reaction and analysis were conducted following the procedure described in Example 12. The results are given in Table 16.

TABLE 16

| | L-valine | |
|---|---|---|
| Nitrile compound | Amount (mg/ml) | Optical purity (% e.e.) |
| isobutyronitrile | 0.8 | 94 |
| glutaronitrile | 0.9 | 100 |
| adiponitrile | 0.1 | 100 |
| n-butyronitrile | 0.6 | 85 |
| methacrylonitrile | 0.3 | 100 |
| crotononitrile | 0.6 | 74 |

Example 17

Three loopfuls of each of the microorganisms given in Table 17 were inoculated to 100 ml of an NBG medium in a 500-ml flask. The flask was oscillated (150 times/minute) at 30° C. for 48 hours to incubate the cells. The cell mass grown by the incubation was collected and washed in the same manner as described in Example 1 and resuspended in a 0.1M $NH_4Cl$—$NH_3$ buffer solution so as to adjust the optical density (OD) at 40. The cell suspension was reacted with 50 μl of DL-2-(N-butylideneamino)pentanenitrile in the same manner as described in Example 12. The results are shown in Table 17.

TABLE 17

| | L-norvaline | |
|---|---|---|
| Strain | Amount (mg/ml) | Optical purity (% e.e.) |
| Rhodococcus sp. BA-1 | 0.1 | 80 |
| Arthrobacter sp. PA-15 | 1.8 | 94 |
| Arthrobacter sp. PC-3 | 1.5 | 91 |

Example 18

Reaction was conducted in the same manner as described in Example 12 except for the addition of 50 μl of DL-2-(N-pentylideneamino)hexanenitrile to 5 ml of the cell suspension of each strain given in Table 18; the cell suspension was prepared according to the procedure described in Example 17. The results are shown in Table 18.

TABLE 18

| | L-norleucine | |
|---|---|---|
| Strain | Amount (mg/ml) | Optical purity (% e.e.) |
| Arthrobacter sp. PA-15 | 0.7 | 84 |
| Arthrobacter sp. PC-3 | 0.5 | 60 |

Example 19

Reaction was conducted in the same manner as described in Example 12 except for the addition of 50 μl of DL-4-methyl-2-(N-3-methylbutylideneamino)pentanenitrile to 5 ml of the cell suspension of each strain given in Table 19; the cell suspension was prepared according to the procedure described in Example 17. The results are shown in Table 19.

TABLE 19

| | L-leucine | |
|---|---|---|
| Strain | Amount (mg/ml) | Optical purity (% e.e.) |
| Arthrobacter sp. PA-15 | 0.6 | 100 |
| Arthrobacter sp. PC-3 | 0.5 | 100 |

Example 20

(1) Preparation of medium:

To 900 g of ion-exchanged water were added 25 g of bouillon [Nutrient Broth No. 2 (Oxoid)] and 10 g of glucose under agitation to prepare Solution A. The Solution A was charged in each of Sakaguchi flasks in an amount of 90 ml and sterilized at 120° C. for 20 minutes in an autoclave. To 100 ml of ion-exchanged water was added 27 g of $Na_2CO_3$ $12H_2O$, and the resultant solution was sterilized at 120° C. for 20 minutes in an autoclave to provide Solution B. In a clean bench, 10 ml of the Solution B was charged in each of the Sakaguchi flasks to prepare a medium.

(2) Incubation and proliferation of cell mass:

To each of the foregoing media were inoculated 3 loopfuls of each of the two strains given below. The resulting medium was incubated under oscillation at 140 rpm at a temperature of 30° C. for 48 hours.

Strains employed:

| Strain | FERM-BP No. |
|---|---|
| Nocardiopsis sp. A10-12 | 2422 |
| Nocardiopsis sp. B9-47 | 2423 |

The cell mass obtained by the incubation was isolated by centrifugation, washed twice with a 0.1M $NH_4Cl$—$NH_3$ buffer solution (pH 10), and then resuspended in a 0.1M $NH_4Cl$—$NH_3$ buffer solution so as to adjust the optical density (OD) at 10.

(3) Reaction:

Into a test tube with an inner diameter of 24 mm was admitted 5 ml of each of the cell suspensions obtained as described above. Then, 50 μl of DL-2-amino-3-methylbutanenitrile was added thereto and the test tube was stoppered. The test tube was shaken at 300 rpm at a temperature of 30° C. for 48 hours.

After completion of the reaction, the reaction mixture was extracted twice with 5 ml of ether, and the water phase thus-obtained was analyzed by HPLC.

The quantity of L-valine thus-formed was determined using Inertsil ODS as a column packing. Its absolute configuration and optical purity were determined similarly by using CHIRALPAK WH. The results are as shown in Table 20.

TABLE 20

| | L-valine | |
|---|---|---|
| Strain | Amount (mg/ml) | Optical purity (% e.e.) |
| Nocardiopsis sp. A10-12 | 1.0 | 96 |
| Nocardiopsis sp. B9-47 | 0.9 | 97 |

Example 21

Into a test tube with an inner diameter of 24 mm was admitted 5 ml of each of the cell suspensions prepared in the manner described in Example 20. Then, 50 μl of DL-2-amino-4-methylpentanenitrile was added thereto and the test tube was stopcocked. The test tube was shaked at 300 rpm at a temperature of 30° C. for 48 hours.

After completion of the reaction, the reaction mixture was extracted twice with 5 ml of ether, and the water phase thus-obtained was analyzed by HPLC.

The quantity of L-leucine thus-formed was determined using Inertsil ODS as a column packing. Its absolute configuration and optical purity were determined similarly by using CHIRALPAK WE. The results are as shown in Table 21.

TABLE 21

| | L-leucine | |
|---|---|---|
| Strain | Amount (mg/ml) | Optical purity (% e.e.) |
| Nocardiopsis sp. A10-12 | 0.8 | 100 |
| Nocardiopsis sp. B9-47 | 1.0 | 100 |

Example 22

Into a test tube with an inner diameter of 24 mm was admitted 5 ml of each of the cell suspensions prepared in the manner described in Example 20. Then, 50 μl of DL-2-amino-pentanenitrile was added thereto and the test tube was stopcocked. The test tube was shaked at 300 rpm at a temperature of 30° C. for 48 hours.

After completion of the reaction, the reaction mixture was extracted twice with 5 ml of ether, and the water phase thus-obtained was analyzed by HPLC.

The quantity of L-norvaline thus-formed was determined using inertsil ODS as a column packing. Its absolute configuration and optical purity were determined similarly by using CHIRALPAK WE. The results are as shown in Table 22.

TABLE 22

| | L-norvaline | |
|---|---|---|
| Strain | Amount (mg/ml) | Optical purity (% e.e.) |
| Nocardiopsis sp. A10-12 | 1.3 | 100 |
| Nocardiopsis sp. B9-47 | 1.4 | 100 |

Example 23

Into a test tube with an inner diameter of 24 mm was admitted 5 ml of each of the cell suspensions prepared in the manner described in Example 20. Then, 50 μl of DL-2-amino-4-hexanenitrile was added thereto and the test tube was stopcocked. The test tube was shaked at 300 rpm at a temperature of 30° C. for 48 hours.

After completion of the reaction, the reaction mixture was extracted twice with 5 ml of ether, and the water phase thus-obtained was analyzed by HPLC.

The quantity of L-norleucine thus-formed was determined using Inertsil ODS as a column packing. Its absolute configuration and optical purity were determined similarly by using CHIRALPAK WE. The results are as shown in Table 23.

TABLE 23

| | L-norleucine | |
|---|---|---|
| Strain | Amount (mg/ml) | Optical purity (% e.e.) |
| Nocardiopsis sp. A10-12 | 0.2 | 84 |
| Nocardiopsis sp. B9-47 | 0.4 | 77 |

Example 24

Into a test tube with an inner diameter of 24 mm was admitted 5 ml of each of the cell suspensions prepared in the manner described in Example 20. Then, 50 μl of DL-2-amino-3-methylbutanenitrile and 60 μl of isobutyraldehyde were added thereto and the test tube was stopcocked. The test tube was shaked at 300 rpm at a temperature of 30° C. for 48 hours.

After completion of the reaction, the reaction mixture was extracted twice with 5 ml of ether, and the water phase thus-obtained was analyzed by HPLC.

The quantity of L-valine thus-formed was determined using Inertsil ODS as a column packing. Its absolute configuration and optical purity were determined similarly by using CHIRALPAK WH. The results are as shown in Table 24.

TABLE 24

| | L-valine | |
|---|---|---|
| Strain | Amount (mg/ml) | Optical purity (% e.e.) |
| Nocardiopsis sp. A10-12 | 2.4 | 97 |
| Nocardiopsis sp. B9-47 | 2.0 | 100 |

Example 25

Into a test tube with an inner diameter of 24 mm was admitted 5 ml of each of the cell suspensions prepared in the manner described in Example 20. Then, 50 μl of DL-2-amino-4-methylpentanenitrile and 60 μl of isovaleraldehyde were added thereto and the test tube was stopcocked. The test tube was shaked at 300 rpm at a temperature of 30° C. for 48 hours.

After completion of the reaction, the reaction mixture was extracted twice with 5 ml of ether, and the water phase thus-obtained was analyzed by HPLC.

The quantity of L-leucine thus-formed was determined using Inertsil ODS as a column packing. Its absolute configuration and optical purity were determined similarly by using CHIRALPAK WE. The results are as shown in Table 25.

TABLE 25

| | L-leucine | |
|---|---|---|
| Strain | Amount (mg/ml) | Optical purity (% e.e.) |
| Nocardiopsis sp. A10-12 | 3.1 | 100 |
| Nocardiopsis sp. B9-47 | 3.5 | 81 |

Example 26

Reaction was conducted in the same manner as described in Example 20, except that 5 ml of each of the suspensions prepared in the manner described in Example 20 was admitted into a test tube with an inner diameter of 24 mm to which 50 μl of DL-2-aminopentanenitrile and 60 μl of n-butyraldehyde were added.

After completion of the reaction, the reaction mixture was extracted twice with 5 ml of ether, and the water phase thus-obtained was analyzed by HPLC.

The quantity of L-norvaline thus-formed was determined using Inertsil ODS as a column packing. Its absolute configuration and optical purity were determined similarly by using CHIRALPAK WE. The results are as shown in Table 26.

TABLE 26

| Strain | L-norvaline | |
|---|---|---|
| | Amount (mg/ml) | Optical purity (% e.e.) |
| Nocardiopsis sp. A10-12 | 3.9 | 95 |
| Nocardiopsis sp. B9-47 | 4.7 | 75 |

Example 27

Reaction was conducted in the same manner as described in Example 20, except that 5 ml of each of the suspensions prepared in the manner described in Example 20 was admitted into a test tube with an inner diameter of 24 mm to which 50 μl of DL-2-aminohexanenitrile and 60 μl of valeraldehyde were added.

After completion of the reaction, the reaction mixture was extracted twice with 5 ml of ether, and the water phase thus-obtained was analyzed by HPLC.

The quantity of L-norleucine thus-formed was determined using Inertsil ODS as a column packing. Its absolute configuration and optical purity were determined similarly by using CHIRALPAK WE. The results are as shown in Table 27.

TABLE 27

| Strain | L-norleucine | |
|---|---|---|
| | Amount (mg/ml) | Optical purity (% e.e.) |
| Nocardiopsis sp. A10-12 | 0.8 | 78 |
| Nocardiopsis sp. B9-47 | 0.7 | 56 |

Example 28

Into a test tube with an inner diameter of 24 mm was admitted 5 ml of each of the cell suspensions prepared in the manner described in Example 20. Then, 50 μl of DL-3-methyl-2-(N-2-methylpropylidene)aminopentanenitrile was added thereto and the test tube was stopcocked. The test tube was shaken at 300 rpm at a temperature of 30° C. for 48 hours.

After completion of the reaction, the reaction mixture was extracted twice with 5 ml of ether, and the water phase thus-obtained was analyzed by HPLC.

The quantity of L-valine thus-formed was determined using Inertsil ODS as a column packing. Its absolute configuration and optical purity were determined similarly by using CHIRALPAK WH. The results are as shown in Table 28.

TABLE 28

| Strain | L-valine | |
|---|---|---|
| | Amount (mg/ml) | Optical purity (% e.e.) |
| Nocardiopsis sp. A10-12 | 1.8 | 97 |
| Nocardiopsis sp. B9-47 | 1.2 | 99 |

Example 29

Reaction was conducted in the same manner as described in Example 28, except that 50 μl of 4-methyl-2-(N-3-methylbutylideneamino)pentanenitrile was added to 5 ml of each of the suspensions prepared in the manner described in Example 20.

After completion of the reaction, the reaction mixture was extracted twice with 5 ml of ether, and the water phase thus-obtained was analyzed by HPLC.

The quantity of L-leucine thus-formed was determined using Inertsil ODS as a column packing. Its absolute configuration and optical purity were determined similarly by using CHIRALPAK WE. The results are as shown in Table 29.

TABLE 29

| Strain | L-leucine | |
|---|---|---|
| | Amount (mg/ml) | Optical purity (% e.e.) |
| Nocardiopsis sp. A10-12 | 1.4 | 100 |
| Nocardiopsis sp. B9-47 | 0.9 | 100 |

Example 30

Reaction was conducted in the same manner as described in Example 20, except that 50 μl of 2-(N-butylideneamino)pentanenitrile was added to 5 ml of each of the suspensions prepared in the manner described in Example 20.

After completion of the reaction, the reaction mixture was extracted twice with 5 ml of ether, and the water phase thus-obtained was analyzed by HPLC.

The quantity of L-norvaline thus-formed was determined using Inertsil ODS as a column packing. Its absolute configuration and optical purity were determined similarly by using CHIRALPAK WE. The results are as shown in Table 30.

TABLE 30

| Strain | L-norvaline | |
|---|---|---|
| | Amount (mg/ml) | Optical purity (% e.e.) |
| Nocardiopsis sp. A10-12 | 3.9 | 91 |
| Nocardiopsis sp. B9-47 | 3.9 | 64 |

Example 31

Reaction was conducted in the same manner as described in Example 20, except that 50 μl of 2-(N-pentylideneamino)hexanenitrile was added to 5 ml of each of the suspensions prepared in the manner described in Example 20.

After completion of the reaction, the reaction mixture was extracted twice with 5 ml of ether, and the water phase thus-obtained was analyzed by HPLC.

The quantity of L-norleucine thus-formed was determined using Inertsil ODS as a column packing. Its absolute configuration and optical purity were determined similarly by using CHIRALPAK WE. The results are as shown in Table 31.

TABLE 31

| | L-norleucine | |
|---|---|---|
| Strain | Amount (mg/ml) | Optical purity (% e.e.) |
| Nocardiopsis sp. A10-12 | 0.2 | 71 |
| Nocardiopsis sp. B9-47 | 0.4 | 100 |

Example 32

(1) Preparation of medium:

To 900 g of ion-exchanged water were added 25 g of bouillon [Nutrient Broth No. 2 (OXOID)] and 10 g of glucose under agitation to prepare Solution A. The Solution A was charged in each of Sakaguchi flasks in an amount of 90 ml and sterilized at 120° C. for 20 minutes in an autoclave. To 100 ml of ion-exchanged water was added 27 g of $Na_2CO_3$ $12H_2O$, and the resultant solution was sterilized at 120° C. for 20 minutes in an autoclave to provide Solution B. In a clean bench, 10 ml of the Solution B was charged in each of the Sakaguchi flasks to prepare a medium.

(2) Incubation and proliferation of cell mass:

To each of the foregoing media were inoculated 3 loopfuls of each of the two strains given below. The resulting medium was incubated under oscillation at 140 rpm at a temperature of 30° C. for 48 hours.
Strains employed:

| Strain | FERM-BP No. |
|---|---|
| Bacillus sp. B9-40 | 3992 |
| Bacillus sp. A9-1 | 3991 |

The cell mass obtained by the incubation was isolated by centrifugation, washed twice with a 0.1M $NH_4Cl$—$NH_3$ buffer solution (pH 10), and then resuspended in a 0.1M $NH_4Cl$—$NH_3$ buffer solution so as to adjust the optical density (OD) at 10.

(3) Reaction:

Into a test tube with an inner diameter of 24 mm was admitted 5 ml of each of the cell suspensions obtained as described above. Then, 50 μl of DL-2-amino-4-methylpentanenitrile was added thereto and the test tube was stopcocked. The test tube was shaked at 300 rpm at a temperature of 30° C. for 48 hours.

After completion of the reaction, the reaction mixture was extracted twice with 5 ml of ether, and the water phase thus-obtained was analyzed by HPLC.

The quantity of L-leucine thus-formed was determined using Inertsil ODS as a column packing. Its absolute configuration and optical purity were determined similarly by using CHIRALPAK WE. The results are as shown in Table 32.

TABLE 32

| | L-leucine | |
|---|---|---|
| Strain | Amount (mg/ml) | Optical purity (% e.e.) |
| Bacillus sp. B9-40 | 0.2 | 100 |
| Bacillus sp. A9-1 | 1.2 | 100 |

Example 33

Into a test tube with an inner diameter of 24 mm was admitted 5 ml of each of the cell suspensions prepared in the manner described in Example 32. Then, 50 μl of DL-2-aminopentanenitrile was added thereto and the test tube was stopcocked. The test tube was shaked at 300 rpm at a temperature of 30° C. for 48 hours.

After completion of the reaction, the reaction mixture was extracted twice with 5 ml of ether, and the water phase thus-obtained was analyzed by HPLC.

The quantity of L-norvaline thus-formed was determined using Inertsil ODS as a column packing. Its absolute configuration and optical purity were determined similarly by using CHIRALPAK WE. The results are as shown in Table 33.

TABLE 33

| | L-norvaline | |
|---|---|---|
| Strain | Amount (mg/ml) | Optical purity (% e.e.) |
| Bacillus sp. B9-40 | 0.9 | 100 |
| Bacillus sp. A9-1 | 1.2 | 100 |

Example 34

Into a test tube with an inner diameter of 24 mm was admitted 5 ml of each of the cell suspensions prepared in the manner described in Example 32. Then, 50 μl of DL-2-aminohexanenitrile was added thereto and the test tube was stopcocked. The test tube was shaked at 300 rpm at a temperature of 30° C. for 48 hours.

After completion of the reaction, the reaction mixture was extracted twice with 5 ml of ether, and the water phase thus-obtained was analyzed by HPLC.

The quantity of L-norleucine thus-formed was determined using Inertsil ODS as a column packing. Its absolute configuration and optical purity were determined similarly by using CHIRALPAK WE. The results are as shown in Table 34.

TABLE 34

| | L-norleucine | |
|---|---|---|
| Strain | Amount (mg/ml) | Optical purity (% e.e.) |
| Bacillus sp. B9-40 | 0.3 | 100 |
| Bacillus sp. A9-1 | 0.3 | 100 |

Example 35

Into a test tube with an inner diameter of 24 mm was admitted 5 ml of each of the cell suspensions prepared in the manner described in Example 32. Then, 50 μl of DL-2-amino-4-methylpentanenitrile and 60 μl of isovaleraldehyde were added thereto and the test tube was stopcocked. The test tube was shaked at 300 rpm at a temperature of 30° C. for 48 hours.

After completion of the reaction, the reaction mixture was extracted twice with 5 ml of ether, and the water phase thus-obtained was analyzed by HPLC.

The quantity of L-leucine thus-formed was determined using Inertsil ODS as a column packing. Its absolute configuration and optical purity were determined similarly by using CHIRALPAK WE. The results are as shown in Table 35.

TABLE 35

| | L-leucine | |
|---|---|---|
| Strain | Amount (mg/ml) | Optical purity (% e.e.) |
| Bacillus sp. B9-40 | 1.0 | 100 |
| Bacillus sp. A9-1 | 2.7 | 100 |

Example 36

Reaction was conducted in the same manner as in Example 32, except that 5 ml of each of the suspensions prepared in the manner described in Example 32 was admitted into a test tube with an inner diameter of 24 mm to which 50 μl of DL-2-aminopentanenitrile and 60 μl of n-butyraldehyde were added.

After completion of the reaction, the reaction mixture was extracted twice with 5 ml of ether, and the water phase thus-obtained was analyzed by HPLC.

The quantity of L-norvaline thus-formed was determined using Inertsil ODS as a column packing. Its absolute configuration and optical purity were determined similarly by using CHIRALPAK WE. The results are as shown in Table 36.

TABLE 36

| | L-norvaline | |
|---|---|---|
| Strain | Amount (mg/ml) | Optical purity (% e.e.) |
| Bacillus sp. B9-40 | 1.2 | 100 |
| Bacillus sp. A9-1 | 3.6 | 100 |

Example 37

Reaction was conducted in the same manner as in Example 32, except that 5 ml of each of the suspensions prepared in the manner described in Example 32 was admitted into a test tube with an inner diameter of 24 mm to which 50 μl of DL-2-aminohexanenitrile and 60 μl of valeraldehyde were added.

After completion of the reaction, the reaction mixture was extracted twice with 5 ml of ether, and the water phase thus-obtained was analyzed by HPLC.

The quantity of L-norleucine thus-formed was determined using Inertsil ODS as a column packing. Its absolute configuration and optical purity were determined similarly by using CHIRALPAK WE. The results are as shown in Table 37.

TABLE 37

| | L-norleucine | |
|---|---|---|
| Strain | Amount (mg/ml) | Optical purity (% e.e.) |
| Bacillus sp. B9-40 | 0.5 | 100 |
| Bacillus sp. A9-1 | 0.9 | 100 |

Example 38

Reaction was conducted in the same manner as in Example 32, except that 5 ml of each of the suspensions prepared in the manner described in Example 32 was admitted into a test tube with an inner diameter of 24 mm to which 50 μl of 4-methyl-2-(N-3-methylbutylideneamino)pentanenitrile was added.

After completion of the reaction, the reaction mixture was extracted twice with 5 ml of ether, and the water phase thus-obtained was analyzed by HPLC.

The quantity of L-leucine thus-formed was determined using Inertsil ODS as a column packing. Its absolute configuration and optical purity were determined similarly by using CHIRALPAK WE. The results are as shown in Table 38.

TABLE 38

| | L-leucine | |
|---|---|---|
| Strain | Amount (mg/ml) | Optical purity (% e.e.) |
| Bacillus sp. B9-40 | 0.3 | 100 |
| Bacillus sp. A9-1 | 0.3 | 100 |

Example 39

Reaction was carried out following the procedure described in Example 32, except that 50 μl of 2-(N-butylideneamino)pentanenitrile was added to 5 ml of each of the cell suspensions prepared in the manner described in Example 32.

After completion of the reaction, the reaction mixture was extracted twice with 5 ml of ether, and the water phase thus-obtained was analyzed by HPLC.

The quantity of L-norvaline thus-formed was determined using Inertsil ODS as a column packing. Its absolute configuration and optical purity were determined similarly by using CHIRALPAK WE. The results are as shown in Table 39.

TABLE 39

| | L-norvaline | |
|---|---|---|
| Strain | Amount (mg/ml) | Optical purity (% e.e.) |
| Bacillus sp. B9-40 | 2.0 | 100 |
| Bacillus sp. A9-1 | 3.6 | 100 |

Example 40

Reaction was carried out following the procedure described in Example 32, except that 50 μl of 2-(N-pentylideneamino)hexanenitrile was added to 5 ml of each of the cell suspensions prepared in the manner described in Example 32.

After completion of the reaction, the reaction mixture was extracted twice with 5 ml of ether, and the water phase thus-obtained was analyzed by HPLC.

The quantity of L-norleucine thus-formed was determined using Inertsil ODS as a column packing. Its absolute configuration and optical purity were determined similarly by using CHIRALPAK WE. The results are as shown in Table 40.

TABLE 40

| | L-norleucine | |
| --- | --- | --- |
| Strain | Amount (mg/ml) | Optical purity (% e.e.) |
| Bacillus sp. B9-40 | 0.2 | 100 |
| Bacillus sp. A9-1 | 0.5 | 100 |

Example 41

Into 100 ml of a medium of pH 7.2 containing 1% glucose, 0.25% $Na_2HPO_4 \cdot 12H_2O$, 0.2% $KH_2PO_4$, 0.05% $MgSO_4 \cdot 7H_2O$, 0.003% $FeSO_4 \cdot 7H_2O$, 0.006% $CaCl_2 \cdot 2H_2O$ and 0.5% isobutyronitrile in a 500-ml shouldered flask was inoculated 4 ml of *Rhodococcus rhodochrous* PA-34 incubated in a medium of pH 7.5 containing 2.5% of Nutrient Broth No. 2 (manufactured by OXOID Co.) and 1% glucose. The cells were cultured at 30° C. for 24 hours. The resulting culture liquid was centrifuged at 10,000 G for 10 minutes to obtain a cell mass, which was then suspended in a 0.1M potassium phosphate buffer solution (pH 7) so as to attain an optical density (OD) of 80.8. The cell suspension (1 ml) was admitted in a test tube, into which 7.0 mg of 2-aminopropionitrile was added. The resultant suspension was shaked at 30° C. for 60 minutes at a rate of oscillation of 150 times per minute. The reaction liquid thus-obtained was centrifuged to remove the cells and then analyzed by HPLC. The analysis has revealed the production of D-alanine with an optical density of 68.1% e.e. in an amount of 0.99 mg.

The determination of the quantity and optical purity of the alanine produced was made by HPLC using CHIRALPAK WE as a column packing.

Example 42

Into 100 ml of a medium of pH 7.2 containing 1% glucose, 0.25% $Na_2HPO_4 \cdot 12H_2O$, 0.2% $KH_2PO_4$, 0.05% $MgSO_4 \cdot 7H_2O$, 0.03% $FeSO_4 \cdot 7H_2O$, 0.006% $CaCl_2 \cdot 2H_2O$, 0.1% yeast extract and 0.5% propionitrile was inoculated one loopful of *Arthrobacter* sp. PC-3, and the cells were cultured at 30 C for 96 hours. The resultant cell culture was centrifuged at 10,000 G for 10 minutes to obtain a cell mass, which was then suspended in a 0.1M potassium phosphate buffer solution so as to attain an optical density (OD) of 75.6. The cell suspension (1 ml) was admitted in a test tube into which 5 mg of 2-amino-2-phenylethanenitrile was charged. The resulting suspension was shaked at 30° C. for 60 minutes at a rate of oscillation of 150 times per minute. The reaction liquid thus-obtained was centrifuged to remove the cells and then subjected to HPLC to analyze D-phenylglycine. As a result, 1.62 mg of D-phenylglycine with an optical purity of 100% e.e. was obtained. The quantity of the phenylglycine produced was determined using Inertsil ODS while the optical purity was measured by using CHIRALPAK WE.

Example 43

A cell mass cultured and collected in the same manner as in Example 42 was suspended in a 2N $NH_4Cl$—$NH_3$ buffer (pH 10.0) in such a way as to attain an OD of 32.4. To 1 ml of this cell suspension was added 5 mg of 2-amino-2-phenylethanenitrile and the resulting suspension was shaked at 60° C. for 60 minutes at a rate of oscillation of 150 times per minute. The reaction liquid thus-obtained was analyzed in the same manner as in Example 42. As a result, it was found that 1.90 mg of D-phenylglycine with an optical purity of 92.7% e.e. was obtained.

We claim:

1. A process for producing an optically active α-amino acid in L-configuration represented by formula (I'):

from the α-aminonitrile compound represented by formula (I):

wherein R is an isopropyl, butyl, or isobutyl group, which process comprises the steps of:

(a) contacting a microorganism having sterospecific nitrilase activity and selected from the group consisting of: Nocardiopsis sp. B96-47, FERM BP-2423; Nocardiopsis sp. A10-12, FERM BP-2422; Bacillus sp. B9-40, FERM BP-3992; and Bacillus sp. A9-1, FERM BP-3991 and the α-aminonitrile in a reaction medium of an ammoniacal buffer solution at a pH in the range of 8–12 to obtain the optically active α-amino acid in L-configuration; and (b) recovering the optically active α-amino acid in L-configuration thus obtained from the reaction medium.

2. A process for producing an optically active α-amino acid in L-configuration represented by formula (I'):

from the α-aminonitrile compound represented by formula (I):

wherein R is an isopropyl, butyl or isobutyl group, which process comprises the steps of:

(a) contacting a microorganism having stereospecific nitrilase activity selected from the group consisting of: *Rhodococcus rhodochrous* PA-34, FERM BP-1559; Rhodococcus sp. AB-16, FERM BP-1555; Rhodococcus sp. BA-1, FERM BP-1557; Mycobacterium sp. AB-43, FERM BP-1556; Arthrobacter sp. PA-15, FERM BP-1558; Arthrobacter sp. PC-3, FERM BP-1560; Nocardiopsis sp. B9-47, FERM BP-2423; Bacillus sp. B9-40, FERM BP-3992; and Bacillus sp. A9-1, FERM BP-3991 and the α-aminonitrile compound in a reaction medium of an ammoniacal buffer solution at a pH in the range of 8–12 in the presence of an aldehyde of formula (I'''):

$$R'-CHO \qquad (I''')$$

wherein R' is an isopropyl, butyl or isobutyl group in a molar ratio in the range of 0.1–10.0 of the α-aminonitrile to the aldehyde to obtain the optically active α-amino acid in L-configuration; and (b) recovering the optically active α-amino acid in L-configuration thus obtained from the reaction medium.

3. A process for producing an optically active α-amino acid in L-configuration of formula (V'):

$$R-CH_2-\underset{\underset{NH_2}{|}}{CH}-COOH \qquad (V')$$

wherein R is an ethyl, propyl, isopropyl, butyl or isobutyl group from the α-(N-alkylideneamino) nitrile compound represented by formula (V):

$$R-CH_2-\underset{\underset{N=CH-R}{|}}{CH}-CN \qquad (V)$$

wherein R is a propyl or butyl group, which process comprises the steps of:

(a) contacting a microorganism having stereospecific nitrilase activity selected from the group consisting of: Rhodococcus sp. PC-29, FERM BP-1561; *Rhodococcus rhodochrous* PA-34, FERM BP-1559; Rhodococcus sp. AB-16, FERM BP-1555; Rhodococcus sp. BA-1, FERM BP-1557; Mycobacterium sp. AB-43, FERM BP-1556; Arthrobacter sp. PA-15, FERM BP-1558; Arthrobacter sp. PC-3, FERM BP-1560; Nocardiopsis sp. A10-12, FERM BP-2422; Nocardiopsis sp. B9-47, FERM BP 2423; Bacillus sp. B9-40, FERM BP-3992; and Bacillus sp. A9-1, FERM BP-3991, and an α-(N-alkylideneamino) nitrile in a reaction medium of an ammoniacal buffer solution, at a pH in the range of 8–12, to obtain the optically active α-amino acid in L-configuration; and (b) recovering the optically active α-amino acid in L-configuration thus obtained from the reaction medium.

4. A process for producing optically active L-α-phenylglycine comprising the steps of:

(a) contacting a microorganism having nitrile-hydrolyzing activity selected from the group consisting of: Rhodococcus sp. PC-29, FERM BP-1561; *Rhodococcus rhodochrous* PA-34, FERM BP-1559; Rhodococcus sp. AB-16, FERM BP-1555; Rhodococcus sp. BA-1, FERM BP-1557; and Mycobacterium sp. AB-43, FERM BP-1556, and 2-amino-2-phenylethanenitrile in a reaction medium at a pH in the range of 8–12 to obtain optically active L-α-phenylglycine; and (b) recovering optically active L-α-phenylglycine thus obtained from the reaction medium.

5. A process as claimed in claim 4, wherein the reaction medium is an ammoniacal buffer solution.

6. A process for producing optically active D-α-phenylglycine comprising the steps of:

(a) contacting Arthrobacter sp. PC-3, FERM BP-1560, and 2-amino-2-phenylethanenitrile in a buffer solution of pH 7 to obtain optically active D-α-phenylglycine; and (b) recovering optically active D-α-phenylglycine thus obtained from the buffer solution.

7. The process of claim 6, wherein the buffer solution is a 0.1M potassium phosphate buffer solution.

8. A process for producing optically active D-α-phenylglycine comprising the steps of:

(a) contacting Arthrobacter sp. PC-3, FERM BP-1560, and 2-amino-2-phenylethanenitrile in a buffer solution of pH 10 to obtain optically active D-α-phenylglycine; and (b) recovering optically active D-α-phenylglycine thus obtained from the buffer solution.

9. A process for producing optically active D-α-alanine comprising the steps of:

(a) contacting *Rhodococcus rhodochrous* PA-4, FERM BP-1559, with 2-aminopropionitrile in a buffer solution of pH 7 to obtain optically active D-α-alanine; and (b) recovering optically active D-α-alanine thus obtained from the buffer solution.

10. The process of claim 9, wherein the buffer solution is a 0.1M potassium phosphate buffer solution.

11. A process for producing L-norvaline of formula (I'):

$$R-\underset{\underset{NH_2}{|}}{CH}-COOH \qquad (I')$$

from the α-aminonitrile compound of formula (I):

$$R-\underset{\underset{NH_2}{|}}{CH}-CN \qquad (I)$$

wherein R is a propyl group,
which process comprises the steps of:

(a) contacting a microorganism selected from the group consisting of: *Rhodococcus rhodochrous* PA-34, FERM BP-1559; Nocardiopsis sp. B9-47, FERM BP-2423; and Nocardiopsis sp. A10-12, FERM BP-2422 and the α-aminonitrile compound in a reaction medium of an ammoniacal buffer solution at a pH in the range of 8–12 to obtain the optically active α-amino acid in L-configuration; and (b) recovering optically active L-norvaline thus obtained from the reaction medium.

12. A process for producing L-norvaline of formula (I'):

$$R-\underset{\underset{NH_2}{|}}{CH}-COOH \qquad (I')$$

from the α-aminonitrile compound of formula (I):

$$R-\underset{\underset{NH_2}{|}}{CH}-CN \qquad (I)$$

wherein R is a propyl group,
which process comprises the steps of:

(a) contacting a microorganism selected from the group consisting of: Rhodococcus sp. PC-29, FERM BP-1561; *Rhodococcus rhodochrous* PA-34, FERM BP-1559; Rhodococcus sp. AB-16, FERM BP-1555; Rhodococcus sp. BA-1, FERM BP-1557; Mycobacterium sp. AB-43, FERM BP-1556; Arthrobacter sp. PA-15, FERM BP-1558; Arthrobacter sp. PC-3, FERM BP-1560; Nocardiopsis sp. A10-12, FERM BP-2422; and Nocardiopsis sp. B9-47, FERM BP-2423 and the α-aminonitrile compound in a reaction medium of an ammoniacal buffer solution at a pH in the range of 8–12, in the presence of an aldehyde of formula (I'''):

$$R-CHO \qquad (I''')$$

wherein R is a propyl group, in a molar ratio in the range of 0.1–10.0 of the α-aminonitrile compound to the aldehyde to obtain the optically active α-amino acid in L-configuration; and (b) recovering an optically active L-norvaline thus obtained from the reaction medium.

13. A process for producing L-valine of formula (V'):

from the α-(N-alkylideneamino) nitrile compound of formula (V):

wherein R is an isopropyl group,
which process comprises the steps of:

(a) contacting a microorganism selected from the group consisting of: Rhodococcus sp. PC-29, FERM BP-1561; *Rhodococcus rhodochrous* PA-34, FERM BP-1559; Rhodococcus sp. AB-16, FERM BP-1555; Rhodococcus sp. BA-1, FERM BP-1557; Mycobacterium sp. AB-43, FERM BP-1556; Arthrobacter sp. PA-15, FERM BP-155; Arthrobacter sp. PC-3, FERM BP-1560; Nocardiopsis sp. A10-12, FERM BP-2422; and Nocardiopsis sp. B9-47, FERM BP-2423 and the α-(N-alkylideneamino)nitrile compound in a reaction medium of an ammonical buffer solution at a pH in the range of 8–12 to obtain the optically active α-amino acid in L-configuration; and (b) recovering optically active L-valine thus obtained from the reaction medium.

14. A process for producing L-leucine of formula (V'):

from the α-(N-alkylideneamino)nitrile compound of formula (V):

wherein R is an isobutyl group,
which process comprises the steps of:

(a) contacting a microorganism selected from the group consisting of: *Rhodococcus rhodochrous* PA-34, FERM BP-1559; Rhodococcus sp. BA-1, FERM BP-1557; Mycobacterium sp. AB-43, FERM BP-1556; Arthrobacter sp. PA-15, FERM BP-1558; Arthrobacter sp. PC-3, FERM BP-1560; Nocardiopsis sp. A10-12, FERM BP-2422; Nocardiopsis sp. B9-47, FERM BP-2423; Bacillus sp. A9-1, FERM BP-3991 and the α-(N-alkylideneamino)nitrile compound in a reaction medium of an ammoniacal buffer solution at a pH in the range of 8–12 to obtain the optically active α-amino acid in L-configuration; and (b) recovering optically active L-leucine thus obtained from the reaction medium.

* * * * *

UNITED STATES PATENT AND TRADEMARK OFFICE
CERTIFICATE OF CORRECTION

PATENT NO. : 5,587,303
DATED : December 24, 1996
INVENTOR(S) : Akiko Wakamoto, et al It is certified that error appears in the above-identified patent and that said Letters Patent is hereby corrected as shown below:

On the title page, Item [75],

Under the title "Assignee", please change "Nippon Mining Company, Ltd., Tokyo, Japan" to --Japan Energy Corporation, Tokyo, Japan--. The recordation date for this change is February 28, 1994 (see enclosed notice of recordation).

In Item [54] and Col. 1, in the title,

Further, please change the title of Patent Number 5,587,303 from "PRODUCTION PROCESS OF L-AMINO ACIDS WITH BACTERIA" to --PRODUCTION PROCESS OF OPTICALLY ACTIVE α-AMINO ACIDS WITH BACTERIA--.

Signed and Sealed this

Twentieth Day of July, 1999

Attest:

Q. TODD DICKINSON

*Attesting Officer*  *Acting Commissioner of Patents and Trademarks*